(12) United States Patent
Leep et al.

(10) Patent No.: US 9,339,034 B2
(45) Date of Patent: May 17, 2016

(54) USE OF THAXTOMIN FOR SELECTIVE CONTROL OF RICE AND AQUATIC BASED WEEDS

(75) Inventors: Daniel C Leep, Lindenhurst, DE (US); Lisa Doricchi, Chesapeake City, MD (US); Maria Julia Perez Baz, Leon (ES); Francisco Romero Millan, Leon (ES); Rosa Isabel Fernandez Chimeno, Leon (ES)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 95 days.

(21) Appl. No.: 12/761,382

(22) Filed: Apr. 15, 2010

(65) Prior Publication Data

US 2010/0267560 A1 Oct. 21, 2010

Related U.S. Application Data

(60) Provisional application No. 61/170,097, filed on Apr. 16, 2009.

(51) Int. Cl.
*A01N 43/60* (2006.01)
*A01P 13/00* (2006.01)

(52) U.S. Cl.
CPC ........................................ *A01N 43/60* (2013.01)

(58) Field of Classification Search
CPC ...................................................... A01N 43/60
USPC ......................................................... 504/136
See application file for complete search history.

(56) References Cited

U.S. PATENT DOCUMENTS

| | | | |
|---|---|---|---|
| 4,990,178 A | 2/1991 | Haneishi | |
| 7,393,812 B2 | 7/2008 | Gerwick | |
| 7,504,244 B2 * | 3/2009 | Szabo et al. | 435/135 |
| 7,989,393 B2 | 8/2011 | Kang | |
| 2004/0102320 A1 | 5/2004 | Grimm | |
| 2004/0192551 A1 | 9/2004 | Bessette | |
| 2008/0248956 A1 * | 10/2008 | Kang et al. | 504/156 |
| 2009/0099022 A1 | 4/2009 | Fernandez | |
| 2010/0167930 A1 | 7/2010 | Koivunen | |

FOREIGN PATENT DOCUMENTS

| | | |
|---|---|---|
| WO | WO 2010078452 | 7/2008 |
| WO | WO2008124675 | 10/2008 |
| WO | WO 2008124675 A2 * | 10/2008 |
| WO | WO 2010066677 | 6/2010 |

OTHER PUBLICATIONS

M.E. Koivunen et al., Evaluation of a New Natural Product Herbicide for Rice Weed Control Marrone Organic Innovations, Inc.,2009 Proceedings of the California Weed Science Society, vol. 61, Jan. 12-14, 2009,cover sheet.*

M.E. Koivunen et al., Evaluation of a New Natural Product Herbicide for Rice Weed Control Marrone Organic Innovations, Inc., 2009 Proceedings of the California Weed Science Society, vol. 61, Jan. 12-14,2009,abstract.*
Taylor, Casoron, A New Aquatic Herbicide [online], Jul. 13, 2007[retrieved on Sep. 27, 2012]. Retrieved from the Internet:<http://web.archive.org/web/20070713111053/http://www.apms.org/japm/vol05/v5p20.pdf>.*
King et al. (J. Agric. Food Chem. 2001, 49, pp. 2298-2301).*
Duke et al.,Pest Management Science, vol. 59, Issue 6-7, Article first published online: May 27, 2003.*
Beausejour "Production of thaxtomin A by Streptomyces scabies strains in plant extract containing media" Can. J. Microbiol. 45: 764-768. 1999.
Duke "Natural products as sources of herbicides: current status and future trends" Weed Res. 40: 99-111. 2000.
Duke "United States Department of Agriculture—Agricultural Research Service research on natural products for pest management" Pest Management Sci 59: 708-717. 2003.
Fry "Thaxtomin A: evidence for a plant cell wall target" Physiolog Molec Plant Pathol 60: 1-8. 2002.
Healy "The txtAB genes of the plant pathogen Streptomyces acidiscabies encode a peptide synthetase required for phytotoxin thaxtomin A production and pathogenicity" Molec. Microbiol. 38: 794-804. 2000.
Hiltunen "Influence of thaxtomins in different combinations and concentrations on growth of micropropagated potato shoot cultures" J. Agric. Food Chem. 54: 3372-3379. 2006.
Hoagland "Microbial allelochemicals and pathogens as bioherbicidal agents" Weed Technol. 15: 835-857. 2001.
King "Isolation and characterizationof phytotoxins associated with Streptomyces scabies" J. Chem. Soc. Chem. Commun. 13: 849-850. 1989.
King "Chemistry of phytotoxins associated with Streptomyces scabies, the causal organism of potato common scab" J. Agric. Food Chem. 40: 834-837. 1992.
King "Herbicidal properties of the thaxtomin group of phylotoxins" J. Agric. Food Chem 49: 2298-2301. 2001.
King "More chemistry of the thaxtomin phytotoxins" Phytochemistry 64: 1091-1096, 2003.
Koivlinen "Evaluation of a new natural product herbicide for rice weed control" Proceedings of the California Weed Science Society 61: 113. 2009.
Loria "Differential production of thaxtomins by pathogenic *Streptomyces* species in vitro" Phytopatholo 85: 537-541. 1995.
Scheible "An arabidopsis mutant resistant to thaxtomin A, a cellulose synthesis inhibitor from *Streptomyces* species" The Plant Cell 15: 1781-1794. 2003.
International Search Report and Written Opinion for PCT App. No. PCT/IB2013/002214 dated Jan. 28, 2014 (14 pages).
Duval et al., "Thaxtomin A Induces Programmed Cell Death in Arabidopsis Thaliana Suspension—Cultured Cells" Planta 222: 820-31. 2006.
Examination Report for NZ App. No. 596336 dated Aug. 23, 2012.
Extended Search Report for EP. App. No. 098371743, dated May 12, 2012.
Examination Report for NZ App. No. 598365, dated Aug. 23, 2012.
Extended Search Report for EP. App. No. 10765219.0, dated Jul. 23, 2012.

(Continued)

*Primary Examiner* — Janet Epps-Smith
*Assistant Examiner* — Courtney Brown
(74) *Attorney, Agent, or Firm* — Ying-Horng Liu; Chainey P. Singleton; Marrone Bio Innovations

(57) ABSTRACT

The use of a bacterial secondary metabolite, thaxtomin is described as an effective herbicide on broadleaved, sedge and grass weeds, e.g., in rice fields with no phytotoxicity to rice as well as on aquatic based weeds.

11 Claims, 2 Drawing Sheets

(56) References Cited

OTHER PUBLICATIONS

International Search Report and Written Opinion dated Aug. 13, 2010 for PCT application serial No. PCT/US2009/069856.
International Preliminary Report on Patentability dated insert date for PCT application serial No. PCT/US2009/069856.
Johnson et al., "Plant-Pathogenic *Streptomyces* Species Produce Nitric Oxide Synthase-Derived Nitric Acid in Response to Host Signals Chemistry" Biology 15: 43-50. 2007.
Office Action (Final Rejection) dated Jan. 19, 2012 for U.S. Appl. No. 12/650,315.
Office Action (Non-Final Rejection) dated Sep. 27, 2012 U.S. Appl. No. 12/650,315.
International Search Report and Written Opinion dated Nov. 11, 2010 for PCT application serial No. PCT/US2010/031317.
International Preliminary Report on Patentability dated Oct. 18, 2011 for PCT application serial No. PCT/US2010/031317.

\* cited by examiner

| Compound | R₁ | R₂ | R₃ | R₄ | R₅ | R₆ |
|---|---|---|---|---|---|---|
| Thaxtomin A (1) | $CH_3$ | OH | $CH_3$ | H | OH | H |
| Thaxtomin A o-isomer (2) | $CH_3$ | OH | $CH_3$ | OH | H | H |
| Thaxtomin C (3) | $CH_3$ | H | H | H | H | H |
| Thaxtomin B (4) | $CH_3$ | OH | $CH_3$ | H | H | H |
| Hydroxythaxtomin C (5) | CH3 | OH | H | H | H | H |
| Thaxtomin A p-isomer (6) | $CH_3$ | OH | $CH_3$ | H | H | OH |
| Hydroxythaxtomin A (7) | $CH_3$ | OH | $CH_3$ | H | OH | OH |
| des-N-methylthaxtomin C (8) | H | H | H | H | H | H |

USE OF THAXTOMIN FOR SELECTIVE CONTROL OF RICE AND AQUATIC BASED WEEDS

PRIORITY CLAIM

This application claims priority under 35 USC 119(e) from application Ser. No. 61/170,097, filed Apr. 16, 2009, the contents of which are incorporated herein by reference.

FIELD OF THE INVENTION

This invention relates to compositions and methods for controlling the germination and growth of broadleaf, sedge and grass weeds, particularly in rice growing systems and/or aquatic based weeds using compounds comprising thaxtomin, a cyclic dipeptide produced by *Streptomyces* sp., as an active ingredient.

BACKGROUND OF THE INVENTION

In the US, direct-seeded rice is grown in sensitive aquatic habitats. Because of this, concerns have been raised on the environmental safety of herbicides used on rice fields, and there is a need for safer and more effective rice herbicides both in conventional and organic rice growing systems. California farmers, who have faced product restrictions due to water quality concerns, report costs of $150/acre for herbicide treatments compared to $35-70/acre for other crops. To date, no selective herbicides are available to control weeds in organic rice. Both broadleaf and grassy weeds in organically grown rice can only be controlled through water management and hence, yield loss in organic rice due to weeds can exceed 50%.

Natural products are substances produced by microbes, plants, and other organisms. Microbial natural products offer an abundant source of chemical diversity, and there is a long history of utilizing natural products for pharmaceutical purposes. However, secondary metabolites produced by microbes can also be successfully used for weed and pest control in agricultural applications.

The best known herbicide derived from a microbial natural product is glufosinate, the synthetic version of phosphinothricin, a breakdown product of bialophos produced by *Streptomyces viridichromogenes* and *Streptomyces hygroscopicus* (Duke, Dayan et al. 2000) and (Hoagland 2001). Hydantoicidin, a nucleotide analog derived from a particular strain of *Streptomyces hygroscopicus* has been the subject of structure-activity and patenting work by agrichemical companies but no commercial products are on the market. (Duke, Dayan et al. 2000). Cornexistin, a nonadride phytotoxin from the basidiomycete *Paecilomyces variotii* has good herbicidal activity against monocotyledonous and dicotyledonous weeds. It appears to be a proherbicide, being converted in vivo to an inhibitor of at least one isozyme of aspartate aminotransferase. (Duke, Dayan et al. 2000). Recently, Dow Agro-Sciences found a compound from two species of fungi isolated by the company Mycosynthetix, a *Fusarium* species and *Nodulosporum* species. The broad spectrum, systemic compound, mevalocidin, kills weeds in 3-4 weeks (Gerwick, (Graupner et al. 2005).

Thaxtomins (4-nitroindol-3-yl-containing 2,5-dioxopiperazines) are a family of dipeptide phytotoxins produced by plant-pathogenic *Streptomyces* sp. (*S. scabies, S. acidiscabies*) that cause scab diseases in potato (*Solanum tuberosum*) (King, Lawrence et al. 1992). Toxin production occurs in diseased tissue and can also be elicited in vitro in an optimal growth medium containing oat bran (Loria, Bukhalid et al. 1995; Beauséjour, Goyer et al. 1999). King and her coworkers (King, Lawrence et al. 2001) demonstrated that all plant pathogenic species in the *Streptomyces* family produce one or more thaxtomins with herbicidal activity. Hiltunen et al. (Hiltunen, Laakso et al. 2006) purified four thaxtomin analogs (thaxtomin A, thaxtomin A ortho isomer, thaxtomin B and thaxtomin D) from cultures of *S. scabies* and *S. turbidiscabies* and showed that all four compounds induced similar symptoms of reduced shoot and root growth, root swelling. (at 10-200 ppb) and necrosis (at 200-1000 ppb) on micropropagated in vitro cultures of potato. In addition thaxtomins applied in combinations, showed additive effects, but no synergism (Hiltunen, Laakso et al. 2006). According to Duke et al. (Duke, Baerson et al. 2003) both thaxtomin A (FIG. 1) and thaxtomin D have marked activity as pre and post emergent, non-systemic herbicides, and concentration of less than 1 uM of thaxtomin A causes cell swelling, necrosis and growth inhibition in mono and dicotyledonous seedlings (Healy. Wach et al. 2000). Thaxtomin has been evaluated as an herbicide by Dow Agro Sciences, Inc., and while active, it lacked systemic action (King, Lawrence et al. 2001). The presence of a nitro group in the indole ring required for an L,L-configuration of the diketopiperazine appears to be the minimal requirement for phytotoxicity. Position of nitro group in the indole ring is very site specific, and the phenyl portion of the phenylalanine plays a necessary role in structural requirements of phytotoxicity (King, Lawrence et al. 1989; King, Lawrence et al. 1992; King, Lawrence et al. 2003). The herbicidal mode of action is based on disruption of cell wall synthesis (Fry and Loria 2002), with inhibition of cellulose biosynthesis being the main target (King et al., 2001; Duval et al., 2005; Johnson et al. 2007). Recently, Kang et al. (Kang, Semones et al. 2008) have described the use of thaxtomin and thaxtomin compositions as algaecides to control algae in water environments.

SUMMARY OF THE INVENTION

The present invention discloses the use of thaxtomin as a pre or post-emergence herbicide against most common weeds in the rice growing systems. It can serve as a safer alternative to synthetic herbicides now on the market. A primary object of the invention is to provide novel herbicidal compositions against both broadleaf, sedge and grassy rice weeds that contain thaxtomin as an active ingredient. Another object is to provide a safe, non-toxic herbicidal composition that does not harm rice (*Oryza sativa* L) and a method that will not harm the environment. The above and other objects are accomplished by the present invention which is directed to herbicidal compositions containing thaxtomin with certain carriers to control the growth of weeds in the rice ecosystem.

The invention is thus directed to a method for modulating growth of monocotyledonous, dicotyledonous and sedge weeds in rice growing systems comprising applying to said weeds or soil in said rice growing system an amount of thaxtomin effective to modulate growth of said weeds. Further, the invention is directed to a method for modulating growth of aquatic based weeds selected from the group consisting of *Ammania* sp., *Alisma plantago-aquatica, Cyperus* sp., *Leptochloa* sp., comprising applying to said aquatic based weeds or soil an amount of thaxtomin or salt thereof effective to modulate said growth of said weeds.

In particular, the invention is directed to an herbicidal composition comprising thaxtomin in an herbicidally effective amount and a carrier and/or diluent, which may optionally be used in modulating growth of monocotyledonous, dicotyledonous and sedge weeds in rice growing systems and/or modulating growth of aquatic based weeds selected from the group consisting of *Ammania* sp. *Alisma plantago-aquatica. Cyperus* sp. *Leptochloa* sp. In a particular embodiment, the composition is an aqueous composition. In another particular embodiment, the thaxtomin in the composition is dissolved in a diluent comprising an organic solvent such as ethanol, isopropanol, or an aliphatic ketone such as acetone, methyl ethyl ketone, methyl isobutyl ketone.

In yet another embodiment, the invention is directed to a method for modulating growth of monocotyledonous, dicotyledonous and sedge weeds comprising applying to said weeds an amount of thaxtomin to modulate growth of said weeds. In a particular embodiment, thaxtomin A is applied in an amount ranging from 0.05 mg/ml to about 0.4 mg/ml. In a more particular embodiment, thaxtomin is produced in fermentation of *S. scabiei* in oat bran broth and partially purified thaxtomin A is applied at a concentration corresponding to 0.065 mg/mL. In a particular embodiment, thaxtomin is applied to the leaves, stems, flowers, foliage and/or roots of said weeds.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Thaxtomin utilized in this invention may be derived in fermentation of following actinomycetes cultures: *S. scabies*—ATCC: 49173, *S. acidiscabies*—ATCC 49003, and *S. scabiei*-BL37-EQ-010- or it can be purchased from commercial sources.

Figure 1:
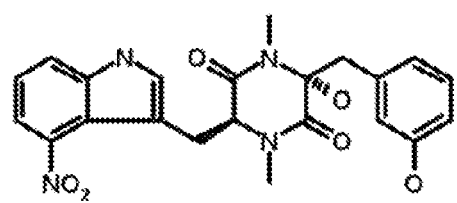
FIG. 1 shows the structure of Thaxtomin A.
Figure 2:
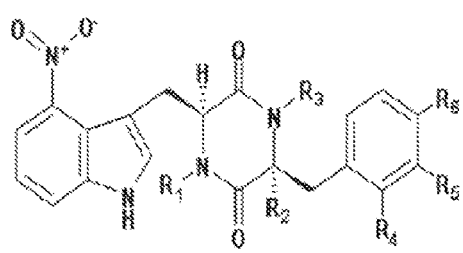
FIG. 2 shows the structure of various Thaxtomin derivatives.

The thaxtomin utilized in the invention include but are not limited to agents described as cyclic dipeptides having the basic structure cyclo-(L-4-nitrotryptophyl-L-phenylalanyl). In embodiments, suitable diketopiperazne moieties may be N-methylated, and include congeners carrying phenylalanyl alpha and ring-carbon hydroxyl groups. Non limiting examples of suitable thaxtomins for use in accordance with the present invention include but are not limited to thaxtominA, thaxtomin A ortho isomer, thaxtomin B, and thaxtomin D and derivatives of any of these (see FIG. 2). The chemical composition comprises:

wherein $R_1$ is methyl or H, $R_2$ is hydroxy or H, $R_3$ is methyl or H, $R_4$ is hydroxy or H, $R_5$ is hydroxy or H, $R_6$ is hydroxy or H, and combinations thereof.

The compositions of the present invention may be sprayed on the plant or applied to the water. Particular embodiments are described in the Examples, infra. These compositions may be in the form of dust, coarse dust, micro granules, granules, wettable powder, emulsifiable concentrate, liquid preparation, suspension concentrate, water degradable granules or oil suspension.

The compositions of the invention do comprise a carrier an/or diluent. The term, 'carrier' as used herein means an inert, organic or inorganic material, with which the active ingredient is mixed or formulated to facilitate its application to plant or other object to be treated, or its storage, transport and/or handling. Examples of diluents or carriers for the post-emergence herbicides include, but are not limited to, water, milk, ethanol, mineral oil, glycerol.

The composition may additionally comprise a surfactant to be used for the purpose of emulsification, dispersion, wetting, spreading, integration, disintegration control, stabilization of active ingredients, improvement of fluidity or rust inhibition. The choice of dispersing and emulsifying agents, such as non-ionic, anionic, amphoteric and cationic dispersing and emulsifying agents, and the amount employed is determined by the nature of the composition and the ability of the agent to facilitate the dispersion of the herbicidal compositions of the present invention.

For post-emergent formulations, the formulation components used may contain smectite clays, attapulgite clays and similar swelling clays, thickeners such as xanthan gums, gum Arabic and other polysaccharide thickeners as well as dispersion stabilizers such as nonionic surfactants (for example polyoxyethylene (20) monolaurate). The concentration of the clays may vary between 0-2.5% w/w of the total formulation, the polysaccharide thickeners may range between 0-0.5% w/w of the total formulation and the surfactants may range between 0-5% w/w of the total formulation.

The composition and method of the present invention will be further illustrated in the following, non-limiting Examples. The examples are illustrative of various embodiments only and do not limit the claimed invention regarding the materials, conditions, weight ratios, process parameters and the like recited herein.

EXAMPLES

The composition and method of the present invention will be further illustrated in the following, non-limiting Examples. The examples are illustrative of various embodiments only and do not limit the claimed invention regarding the materials, conditions, weight ratios, process parameters and the like recited herein.

Example 1

In the first study, thaxtomin A derived from a marine actinomycete BL37-EQ2-010 was tested from 64 to 1000 g a.i. per hectare and showed excellent (95-0.100%) control of *Ammania* species, Ducksalad and *Cyperus difformis*. Thaxtomin also exhibited complete safety to transplanted rice at all rates tested, while only slight growth reductions to direct-seeded rice were observed at rates up to 750 g a.i. per hectare. At higher rates (500-1000 g a.i. per hectare), thaxtomin A also displayed 90-100% control of *Echinochloa colonum* with moderate activity on barnyardgrass.

Example 2

In a second pot study test in greenhouse conditions, treatments of thaxtomin A at 500 g a.i. per hectare showed 100% control of *Monorhoria vaginalis*, spp., *Heteranthem limosa*, *Cyperus difformis*, *Sphenoclea zeylanica*, *Alisma-plamago aquatica* and *Cyperus iria* with excellent rice selectivity on transplanted 'M202' Japonica-type rice, along with minimal growth inhibition (15%) to direct-seeded rice.

At 500 g a.i. per hectare, the perennial species *Marsilea quadrifolia* and *Eleocharis dulcis* also displayed moderate to very good weed suppression, from 70 to 85%, respectively. The activity on susceptible and resistant biotypes of *Scirpus mucronatus* was somewhat weaker (70 to 75%) than that observed for other sedge weeds in this study.

At 250 g a.i. per hectare, thaxtomin A exhibited 95 to 100% control of previously confirmed resistant biotypes of *Ammania* spp., *Cyperus difformis* and *Alisma planiago-aquatica*. Thaxtomin showed weakness on most of the *Echinochloa* spp. up to the highest rate tested; 1000 g a.i. per hectare. Moderate suppression (60%) was noted on *Echinochloa colonum* at 500 g a.i. per hectare.

At the highest rate tested; 1000 g a.i., Thaxtomin displayed excellent selectivity on transplanted rice, while providing 85 to 100% control of all annual and perennial broadleaf and sedge weeds, including resistant biotypes. Direct-seeded rice exhibited 40% growth inhibition at this rate. The results presented in Table 1 suggest that Thaxtomin is an effective weed management tool in rice.

TABLE 1

| Weed control by thaxtomin A expressed as % control (weeds) or effect on crop growth (rice) | | | | | | | | | | | | | | | | |
|---|---|---|---|---|---|---|---|---|---|---|---|---|---|---|---|---|
| Rate g/ha | DSR | TPL | CYI | LEF | MAQ | BYG | EO2 | ECC | MON | AMM | DSA | CPD | SCM | SPZ | WPL | WCN |
| | RICE | | | | | | BROADLEAF, SEDGE, GRASS | | | | | | | | | |
| 64 | 10 | 0 | 45 | 0 | 20 | 0 | 0 | 0 | 0 | 0 | 0 | 0 | 0 | 0 | 0 | * |
| 125 | 10 | 0 | 45 | 50 | 25 | 0 | 0 | 0 | 100 | 30 | 100 | 85 | 30 | 90 | 70 | 35 |
| 250 | 10 | 0 | 95 | 60 | 40 | 15 | 20 | 35 | 100 | 90 | 100 | 100 | 30 | 90 | 95 | 85 |
| 500 | 15 | 0 | 100 | 70 | 70 | 30 | 20 | 60 | 100 | 100 | 100 | 100 | 70 | 100 | 100 | 85 |
| 1000 | 40 | 10 | 100 | 100 | 85 | 40 | 30 | 60 | 100 | 100 | 100 | 100 | 95 | 100 | 100 | 95 |

* Variable germination- ratings could not be determined

Example 3

A pot study was conducted to test the phytotoxicity of thaxtomin A on broadleaved, sedge and grass weeds. Seeds of two most common broadleaf (redstem; *Ammannia* spp. and common waterplantain; *Alisma plantago-aquatica*), sedge (smallflower umbrella sedge; *Cyperus diiformis*) and grass (sprangletop: *Leptochloa uninervia*) weeds each were planted in a plastic pots filled with heavy clay soil. The less than 1-inch tall plants grown under growth lights (12-h light/12-h dark) at 28° C. were sprayed with pure thaxtomin A solutions containing 0.05, 0.1, 0.2, and 0.4 mg thaxtomin A per mL of solvent (4% ethanol and 0.2% non-ionic surfactant). A solution of 4% ethanol+0.2% non-ionic surfactant without thaxtomin A was used as a control treatment. Same treatments were applied to three-inch tall rice plants grown submerged under growth lights at 28° C. Three different varieties of rice exhibiting different grain lengths and growth periods were used (S102, M104, M206). All treatments were applied in three replicates. Treated plants were kept at 28° C. under growth lights and observed at three time points—5, 12 and 21 days after treatment—for visual symptoms of phytotoxicity and % control.

Symptoms of phytotoxicity were visible in the plants treated with solutions of high thaxtomin A content five days after the treatment. The % weed control obtained with different concentrations of thaxtomin is listed in Tables 2A and 2B. At each evaluation time point, no phytotoxicity was observed in any of the three rice cultivars treated with increasing concentrations of thaxtomin A.

Tables 2A and 2B. Effect of increasing concentration of thaxtomin A on the control of the four most common rice weeds in California. In each column, numbers that are marked with different letters are statistically different from each other at p<0.05.

TABLE 2A

| Thaxtomin (mg/mL in | *Ammania* sp (% control) | | | *Alisma plantago-aquatica* (% control) | | |
|---|---|---|---|---|---|---|
| 4% ethanol) | 5 DAYS | 12 DAYS | 21 DAYS | 5 DAYS | 12 DAYS | 21 DAYS |
| 0 | 0 | 0a | 0a | 0a | 0a | 0a |
| 0.05 | 0 | 0a | 63b | 8a | 40b | 83b |
| 0.1 | 0 | 0a | 53b | 28ab | 43b | 70b |
| 0.2 | 0 | 0a | 70b | 40b | 87c | 100c |
| 0.4 | 0 | 3b | 75b | 62b | 87c | 98c |

TABLE 2B

| Thaxtomin (mg/mL in | *Cyperus* sp (% control) | | | *Leptochloa* sp (% control) | | |
|---|---|---|---|---|---|---|
| 4% ethanol) | 5 DAYS | 12 DAYS | 21 DAYS | 5 DAYS | 12 DAYS | 21 DAYS |
| 0 | 0a | 0a | 0a | 0 | 0a | 0a |
| 0.05 | 5a | 15a | 53b | 0 | 0a | 0a |
| 0.1 | 12a | 75b | 90c | 0 | 2a | 3a |
| 0.2 | 16a | 77b | 88c | 0 | 10b | 12a |
| 0.4 | 25a | 73b | 83c | 0 | 10b | 17a |

Thaxtomin A at 0.2 mg/ml, resulted in complete control of common water plantain (*Alisma plantago-aquatica*) used as a representative of a common broadleaf weed in rice. Thaxtomin A was slightly less effective in controlling red stem (*Ammania* sp.) and sedge (*Cyperus difformis*) for which the highest concentration (0.4 mg/mL) resulted in about 75-80% control. Thaxtomin A resulted only in partial control of sprangletop (*Lemochloa* sp.)—with only 17% control with the highest concentration (0.4 mg/mL).

Example 4

A strain of *S. scabiei* (BL37-EQ2-010) was grown in oat bran broth for 5 days (25° C., 200 rpm). The whole cell broth with a thaxtomin A concentration of 4.3 ug/mL, was extracted using XAD resin. The dried crude extract was resuspended in 4% ethanol and 0.2% non-ionic surfactant at a concentration of 10 mg/mL, and the solution with approximately 0.065 mg thaxtomin A per mL, was tested on four weed species (red-stem: *Ammania* spp., common waterplantain; *Alisma plantago-aquatica*), smallflower umbrella sedge; *Cyperus difformis* and sprangletop: *Leptochloa uninervia*), each in three replicates. Treated plants were kept in a greenhouse under 12 h light/12 h dark conditions. Data from the evaluations at three time points: 5, 12 and 21 days after treatment are presented in Table 3.

TABLE 3

Weed control efficacy of a *S. acidiscabies* extract containing thaxtomin A on four different rice weed species. Letters in each column indicate statistically significant differences at $p < 0.05$.

| Species | 5 DAYS % control | 12 DAYS % control | 21 DAYS % control |
|---|---|---|---|
| Control (for all species) | 0a | 0a | 0a |
| *Ammania* sp. | 0a | 0a | 87b |
| *Alisma plantago-aquatica* | 18a | 68b | 82b |

TABLE 3-continued

Weed control efficacy of a *S. acidiscabies* extract containing thaxtomin A on four different rice weed species. Letters in each column indicate statistically significant differences at $p < 0.05$.

| Species | 5 DAYS % control | 12 DAYS % control | 21 DAYS % control |
|---|---|---|---|
| *Cyperus difformis* | 15a | 72b | 72b |
| *Leptochloa uninervia* | 7a | 8a | 10a |

It appears that the extract from a bacterial culture of *S. acidiscabies* showed good efficacy (>70%) against three of the most common weed species in California rice fields. At this extract concentration, the efficacy against sprangletop (*Leptochloa uninervia*) was not satisfactory. The herbicidal effect of the thaxtomin-containing extract was slower on red stem than on any other weeds tested in this study.

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

CITED REFERENCES

Beauséjour, J., C. Goyer, et al. (1999). "Production of thaxtomin A by *Streptomyces* strains in plant extract containing media." *Can J Microbial* 45: 764-768.

Duke, S. O., S. R. Baerson, et al. (2003). "United States Department of Agriculture-Agricultural Research Service research on natural products for pest management." *Pest Manag Sci* 59: 708-717.

Duke, S. O., F. E. Dayan, et al. (2000). "Natural products as sources of herbicides: current status and future trends." *Weed Research* 40: 99-111.

Fry, B. A. and R. Loria (2002). "Thaxtomin A: Evidence for a plant cell wall target." *Physiological and Molecular Plant Pathology* 60: 1-8.

Gerwick, B. C., P. R. Graupner, et al. (2005). Methylidene mevalonates and their use as herbicides. U.S. Pat. No. 7,393,812: 16.

Healy. F. O., M. J. Wach, et al. (2000). "The txtAB genes of the plant pathogen *Streptomyces acidiscabies* encode a peptidesynthetase required for phytotoxin thaxtomin A prodcution and pathogenicity." *Molecular Microbiology* 38: 794-804.

Hiltunen, L. H., I. Laakso, et al. (2006). "Influence of thaxtomins in different combinations and concentrations on growth of micropropagated potato shoot cultures." *J Agric Food Chem* 54: 3372-3379.

Hoagland, R. E. (2001). "Microbial allelochemicals and pathogens as bioherbicidal agents." *Weed Technology* 15: 835-857.

Kang, Y., S. Semones, et al. (2008). Methods of controlling algae with thaxtomin and thaxtomin compositions. USA, Novozymes Biologicals, Inc.

King, R. R., C. H. Lawrence, et al. (1992). "Chemistry of phytotoxins associated with *Streptomyces scabies*, the causal Organism of potato common scab." *J. Agric. Food Chem* 40: 834-837.

King, R. R., C. H. Lawrence, et al. (1989). "Isolation and characterization of phytotoxin associated with *Streptomyces scabies*." *Journal of the Chemical Society. Chemical Communications* 13: 849-850.

King, R. R., C. H. Lawrence, et al. (2003). "More chemistry of the thaxtomin phytotoxins." *Phytochemistry* 64: 1091-1096.

King, R. R., C. H. Lawrence, et al. (2001). "Herbicidal properties of the thaxtomin group of phytotoxins." *J Agric Food Chem* 49: 2298-2301.

Loria, R., R. A. Bukhalid, et al. (1995). "Differential production of thaxtomins by pathogenic *Streptomyces* species in vitro" *Phytopathology* 85: 537-541.

What is claimed is:

1. A method for inhibiting post-emergent growth of monocotyledonous, dicotyledonous and sedge weeds in rice growing systems comprising
    applying to said monocotyledonous, dicotyledonous and sedge weeds in said rice growing system an amount ranging from 0.05 to 4.0 mg/ml of thaxtomin to inhibit growth of said monocotyledonous, dicotyledonous and sedge weeds, wherein said monocotyledonous, dicotyledonous and sedge weeds comprise *Ammania* sp., *Alisma plantago-aquatica, Cyperus* sp., *Leptochloa* sp. or a combination thereof.

2. The method according to claim 1, wherein the thaxtomin has the following composition

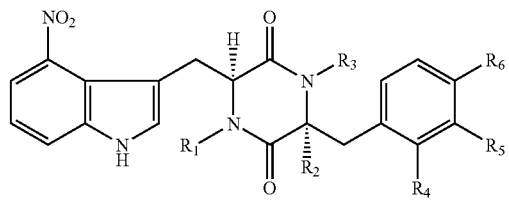

wherein R1 is methyl or H, R2 is hydroxy or H, R3 is methyl or H, R4 is hydroxy or H, R5 is hydroxy or H, R6 is hydroxy or H, and combinations thereof.

3. The method according to claim 1, wherein said thaxtomin is thaxtomin A, thaxtomin A ortho isomer, thaxtomin B, or thaxtomin D or derivatives thereof.

4. A method for inhibiting post-emergent growth of aquatic based weeds comprising the steps of;
    providing aquatic based weeds selected from the group consisting of *Ammania* sp., *Alisma plantago-aquatica, Cyperus* sp., and *Leptochloa* sp.; and
    applying to said aquatic based weeds an amount ranging from 0.05 to 4.0 mg/ml of thaxtomin or salt thereof to inhibit said growth of said aquatic based weeds.

5. The method according to claim 4, wherein the thaxtomin has the following composition

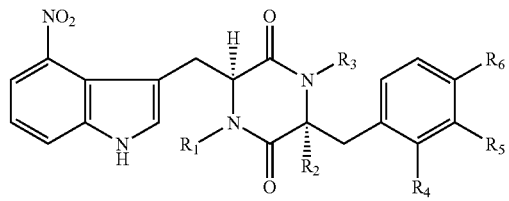

wherein R1 is methyl or H, R2 is hydroxy or H, R3 is methyl or H, R4 is hydroxy or H, R5 is hydroxy or H, R6 is hydroxy or H, and combinations thereof.

6. The method according to claim 4, wherein said thaxtomin is thaxtominA, thaxtominA ortho isomer, thaxtomin B, or thaxtomin D or derivatives thereof.

7. The method according to claim 1, wherein said thaxtomin is derived from actinomycete BL37-EQ2-010.

8. The method according to claim 4, wherein said thaxtomin is derived from actinomycete BL37-EQ2-010.

9. A method for inhibiting post-emergent growth of monocotyledonous, dicotyledonous and sedge weeds in rice growing systems comprising
    providing a thaxtomin composition;
    providing a rice growing system comprising post-emergent growth of one or more aquatic based weeds selected from the group consisting of *Ammania* sp., *Alisma plantago-aquatica, Cyperus* sp., and *Leptochloa* sp.;
    applying to said one or more aquatic based weeds in said rice growing system an amount ranging from 0.05 to 4.0 mg/ml of thaxtomin to inhibit growth of said one or more aquatic based weeds.

10. The method according to claim 9, wherein said thaxtomin composition is thaxtominA, thaxtominA ortho isomer, thaxtomin B, or thaxtomin D or derivatives thereof.

11. The method according to claim 9, wherein the thaxtomin has the following composition

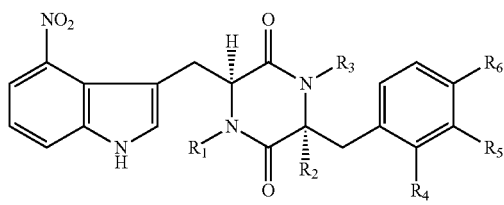
wherein
R1 is a methyl, R2 is a hydroxy, R3 is a methyl, R4 is a hydroxy, R5 is a H, R6 is a H;
R1 is a methyl, R2 is a hydroxy, R3 is a H, R4 is a H, R5 is a H, R6 is a H;
R1 is a methyl, R2 is a hydroxy, R3 is a methyl, R4 is a H, R5 is a H, R6 is a hydroxy;
R1 is a methyl, R2 is a hydroxy, R3 is a methyl, R4 is a H, R5 is a hydroxy, R6 is a hydroxy; or
R1 is a H, R2 is a H, R3 is a H, R4 is a H, R5 is a H, R6 is a H.
\* \* \* \* \*